(12) United States Patent
Nielsen et al.

(10) Patent No.: US 9,317,941 B2
(45) Date of Patent: Apr. 19, 2016

(54) METHOD OF IMAGE RECONSTRUCTION FOR A FILTERED BACK PROJECTION IN LIMITED ANGLE TOMOGRAPHY

(75) Inventors: Tim Nielsen, Hamburg (DE); Sebastian Hitziger, Eindhoven (NL); Michael Grass, Buchholz In der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 87 days.

(21) Appl. No.: 14/344,230

(22) PCT Filed: Aug. 27, 2012

(86) PCT No.: PCT/IB2012/054367
§ 371 (c)(1),
(2), (4) Date: Mar. 11, 2014

(87) PCT Pub. No.: WO2013/038283
PCT Pub. Date: Mar. 21, 2013

(65) Prior Publication Data
US 2014/0348407 A1 Nov. 27, 2014

Related U.S. Application Data

(60) Provisional application No. 61/533,311, filed on Sep. 12, 2011.

(51) Int. Cl.
*G06K 9/00* (2006.01)
*G06T 11/00* (2006.01)
*A61B 6/03* (2006.01)

(52) U.S. Cl.
CPC ............... *G06T 11/006* (2013.01); *A61B 6/035* (2013.01); *G06T 2210/41* (2013.01); *G06T 2211/421* (2013.01); *G06T 2211/436* (2013.01)

(58) Field of Classification Search
None
See application file for complete search history.

(56) References Cited

U.S. PATENT DOCUMENTS

| 6,987,829 | B2 | 1/2006 | Claus | |
|---|---|---|---|---|
| 2007/0036418 | A1* | 2/2007 | Pan et al. | 382/131 |
| 2007/0053556 | A1 | 3/2007 | Nielsen et al. | |
| 2007/0093711 | A1 | 4/2007 | Hoheisel et al. | |
| 2009/0310844 | A1* | 12/2009 | Ludwig et al. | 382/131 |
| 2012/0039433 | A1* | 2/2012 | Berkus et al. | 378/8 |

(Continued)

OTHER PUBLICATIONS

Mertelmeier et al (NPL: "Optimizing filtered backprojection reconstruction for a breast tomosynthesis prototype device" SPIE vol. 6142, 61420F, (2006)).*

(Continued)

*Primary Examiner* — Bhavesh Mehta
*Assistant Examiner* — Oneal R Mistry

(57) ABSTRACT

The present invention is directed to a limited angle tomography in combination with a filtered back projection using a special filter operator X. The filter operator X used within the present invention makes it possible to perform region of interest reconstructions although delivering high quality reconstruction images as generated by high effort SART methods. The used filter operator is purely and solely mathematically determined and defined by the spatial geometry which is used for the limited angle tomography. Without having the need to perform several iterations, the present invention directly calculates a solution, i.e. reconstructed image, equivalent to known iteratively construction methods. Although, incomplete projection data p may only be used, the present invention provides for a high image quality.

13 Claims, 7 Drawing Sheets

(56) References Cited

U.S. PATENT DOCUMENTS

2012/0128120 A1* 5/2012 De Man et al. ................ 378/16
2012/0207370 A1* 8/2012 Fahimian ............... A61B 6/032
382/131

OTHER PUBLICATIONS

Jerebco et al: "Evaluation and Optimization of the Maximum-Likelihood Approach for Image Reconstruction in Digital Breast Tomosynthesis"; Progress in Biomedical Optics and Imaging, 2010, vol. 11 (1), pp. 76220E1-76220E-9.

Ludwig et al: "A Novel Approach for Filtered Backprojection in Tomosynthesis Based on Filter Kernels Determined by Iterative Reconstruction Techniques"; Lecture Notes in Computer Science, 2008, vol. 5116, pp. 612-620.

Saito et al: "High Quality CT Image Reconstruction From a Small Number of Projections"; Department of Electical Communications, Tohoku University, Japan, IEEE, 1988, pp. 1272-1275.

Gao et al: "An Extapolation Method for Image Reconstruction From a Straight-Line Trajectory"; Nuclear Science Symposium Conference Record, IEEE, 2006, pp. 2304-2308.

Clackdoyle et al: "Quantitative Reconstruction From Truncated Projections"; 2003 IEEE Nuclear Science Symposium Conference Record, Oct. 2003, pp. 2036-2038.

Cho et al: "Cone-Beam CT From Width-Truncated Projections"; Comptuerized Medical Imaging and Graphics, Pergamon Press, vol. 20, No. 1, Jan. 1996, pp. 49-57.

Kazantsev: :Tomographic Artefacts Suppression Via Backprojection Operator Optimization; Proceedings of the International Conference on Image Processing Lausanne, IEEE, Sep. 1996, vol. 1, pp. 749-751.

Kak et al: "Prinicples of Computerized Tomography"; Chapter 3, IEEE Press, 1999.

Lewitt et al: "Processing of Incomplete Measurement Data in Computed Tomography"; Medical Physics, 1979, vol. 6, Issue 5, pp. 412-417.

* cited by examiner

US 9,317,941 B2

METHOD OF IMAGE RECONSTRUCTION FOR A FILTERED BACK PROJECTION IN LIMITED ANGLE TOMOGRAPHY

CROSS-REFERENCE TO PRIOR APPLICATIONS

This application is the U.S. National Phase application under 35 U.S.C. §371 of International Application No. PCT/IB2012/054367, filed on Aug. 27, 2012, which claims the benefit of U.S. Provisional Patent Application No. 61/533311, filed on Sep. 12, 2011. These applications are hereby incorporated by reference herein.

FIELD OF THE INVENTION

The invention relates to filtered back projection. In particular the invention relates to a method of image reconstruction for a filtered back projection in limited angle tomography, a calculating device, a computer-readable medium and a program element.

BACKGROUND OF THE INVENTION

Image reconstruction has become more and more important in the last few years especially in the field of medical imaging. Limited angle tomography is increasingly applied in interventional and diagnostic X-ray imaging. Examples are interventional C-arm systems using acquisitions at reduced angular range, mammography tomosynthesis or tomosynthesis for RAD applications. In addition, gating signals representing breathing or cardiac motion are used to reduce the angular range available for reconstruction. In case of limited angular range, iterative reconstruction is a very flexible reconstruction which can be applied. For example algebraic reconstruction techniques (ART), simultaneous algebraic reconstruction techniques (SART) or simultaneous iterative reconstruction technique (SIRT) may be mentioned. Prior knowledge to regularize the reconstruction can be included. One of the disadvantages of iterative reconstruction is its high computational effort and the inability to perform region of interest (ROI) reconstructions. For example US 2007/0053556 A1 and US 2007/0093711 A1 describe iterative data reconstruction methods.

As a technically different variant filtered back projection (FBP) is used in the art in order to reconstruct images. In the known FBP art the mathematically exact filters derived for complete data acquisition e.g. from computer tomography (CT) geometries are adapted for FBP when being applied to limited angle tomography. This may be based on individual impressions of reconstruction results in the reconstructed images. Such filters may be seen as heuristically generated filters. Thus, FBP methods use adapted filters which aim to reduce the effects of the insufficient projection acquisition and to generate image impressions which are advantageous for the clinical application target of the limited angle tomography. However, the filter derivation is not mathematically consistent and may therefore lead to image reconstruction results which are worse compared to the known iterative methods when applied to an incomplete data set.

Furthermore the known methods of filtered back projection (FBP) are not straight forward applicable to an incomplete projection data set like for example a limited angle tomography data set. For example a breast screening may only use an angular range of +/−10°, which results in an absolute angular range of 20°. This complicates image reconstruction.

SUMMARY OF THE INVENTION

There may be a need to provide for a fast and high quality image reconstruction of a limited angle tomography data set. There may be a further need for the provision of reconstruction results equivalent to iterative reconstruction while at the same time enabling region of interest reconstruction.

The present invention meets said needs. The object of the present invention is to provide for an improved image reconstruction.

The object of the present invention is solved by the subject-matter of the independent claims. Further embodiments and advantages of the invention are incorporated in the dependent claims.

The described embodiments similarly pertain to the method of image reconstruction for a filtered back projection in limited angle tomography, the calculating device for image reconstruction for a filtered back projection in limited angle tomography, the computer-readable medium and the program element. Synergetic effects may arise from different combinations of the embodiments although they might not be described in detail.

Further on, it shall be noted that all embodiments of the present invention concerning a method, might be carried out with the order of the steps as described, nevertheless this has not to be the only and essential order of the steps of the method. All different orders and combinations of the method steps are herewith described.

In the context of the present invention limited angle tomography projection data p was/were generated with a tomography using less than 180° around the object like e.g. a human breast which is analyzed with the tomography.

In the context of the present invention, the term "filter" shall be understood as a filter operator which is calculated analytically based on the number of projections comprised by the projection data p and/or the covered angular range of the limited angle tomography by means of which the data p were generated. Also other geometrical parameters of the tomography may be used to define or describe said geometry.

According to an exemplary embodiment of the invention, a method of image reconstruction for a filtered back projection in limited angle tomography is presented. The presented method comprises the steps of obtaining projection data p of an object O, wherein the projection data p describe N projections of the object O, which N projections were generated with the certain tomography geometry of a limited angle tomography. Furthermore, the method comprises the step of applying a filter operator X to the projection data p to generate filtered projection data Xp, wherein Xp describe N filtered projections of the object O and wherein X is determined in such a way that each filtered projection is calculated from all N projections of the data p. Furthermore the method defines the step of calculating a back projection of the filtered projection data Xp using a back projection operator B to generate a reconstructed image B(Xp).

In other words the filtered projection data Xp describe N filtered projections. Each of these filtered projections is calculated from all projections of the limited angle tomography data set p by applying the filter X to each of these projections before combining them into each filtered projection. In this way, each filtered projection depends on all other projections which have been acquired as a part of this limited angle tomography projection data set.

The presented method provides for a higher stability against noise and provides for a correct consideration of redundant data.

Therein filter X may be configured in such a way that Xp describe N filtered projections of the object and wherein each filtered projection is calculated from all N projections of the data p. Therein the projection data p are to be understood as limited angle tomography projection data p. Furthermore N is an integer like e.g. 1, 2, 3, 4, and so on.

For detecting that the presented method of the present invention is used the following should be noted. In case a given data set p only comprises one projection containing data and all other projections contain 0 the presented method provides an image with a certain feature. For directions which are associated with the projections containing only 0, the method of the present invention adds high and low frequency information. In contrast to that the prior art methods are only able to provide in this case for low frequency information or 0. This will become clearer in the context of the below description.

The filter operator X used by the present invention ensures that all N projections or views that are comprised by the data p are used in order to generate the filtered data Xp. This will become clearer in the context of the following description in which the generation and use of X will be explained in detail.

In contrast to the mentioned prior art reconstruction, the present invention does not need several iteration steps. The application of the filter operator X to the projection data p as well as forming a back projection with the back projection operator B needs only one iteration, the back projection, and thus provides for a direct solution of the underlying mathematical problem. In other words, the present invention provides for a direct and non-iterative way of reconstructing an image by means of a unique and advantageous filter operator X.

In other words, a filter back projection method is presented which uses a very special filter operator X. The presented method makes use of the circumstance that in limited angle tomography special trajectories of the radiative source relative to the detector may advantageously be used. For example, if said trajectory is defined to lay inside a plane which is perpendicular to the plane that is defined by the detector elements, the filter operator X, as defined in the present invention, provides for several advantages for an accelerated image reconstruction with a comparable quality compared to known reconstructions. The filter operator X may, for example, be embodied as $(PB)^+$, but also other filter operators X are possible which depend on the limited angle tomography geometry.

Consequently, by means of choosing or determining the certain tomography geometry for generating the projection data p, the filter operator X of the present invention is already mathematically defined. The filter operator X may be calculated analytically and may only depend on the certain tomography geometry like the number of projections taken during a limited angle tomography and like the covered angular range of the limited angle tomography. All parameters, which define the geometry of the data generation determine the filter generation. These art from and size of the detector, number of positions of the source from which positions projections are generated, the exact posture or of each position of source relative to the detector and the maximal height of the projected object above the detector.

The filter X may be calculated once and then being used to reconstruct all data sets acquired with the same projection geometry. This may generate an advantage in time.

For example, a medical device or especially a tomography device or a calculation unit according to the present invention may calculate filter operator X based on solely the geometry data of the limited angle tomography.

Therein the term "using a back projection operator B to generate a reconstruction image B(Xp)" shall be understood as generating a reconstructed image B(Xp) by means of applying back projection operator B to the filter projection data Xp. In other words the filtered projections Xp are back projected to the reconstruction volume.

The filter operator X which may be entirely mathematically defined by the geometry which was used for generating the data p may be embodied in various ways. For example, the filter operator X is embodied as a composition of a projection operator data P and a back projection operator B. Such a composed operator PB may be additionally transformed in order to form it to generalize inverse composition operator $(PB)^+$. As it will be described later on, such a composition operator PB provides for several advantages of the present invention.

According to another exemplary embodiment filter operator X is embodied as generalized inverse operator $(PB)^+$.

Thus X may be composed of the back projection operator B and the corresponding adjoint projection operator P.

In other words, the filter operator X can be derived by imposing on the image f to be reconstructed under the condition to be in agreement with the projection data p generated with the tomography. This condition is described by the equation Pf=p. In general, more than one solution f fulfilling this condition exists. The one with minimal norm is given by f=P+p, where P+ is the generalized inverse of P. Due to the relation of P and B being adjoint operators as explained below, this solution can be rewritten as f=B(PB)+p. Hence, when the filter operation X is chosen as (PB)+, the solution f=B(Xp) fulfils the condition to be in agreement with the projection data.

The embodiment of the filter operator $(PB)^+$ allows for advantageously obtaining an image f that is in agreement with all the projection data p, i.e. an image f fulfilling the equation Pf=p. This is explained in the following.

First, the generalized inverse, also known as Moore-Penrose pseudoinverse, is defined for this purpose. For a linear operator P, the generalized inverse operator $P^+$ can be defined as the operator assigning to any p the minimal norm solution $f^+$ of the linear equation Pf=p with unknown f. The minimal norm solution is defined as the unique solution with minimal norm to said equation. Hence, in the case of p denoting the measured projection data, the minimal norm solution $f^+=P^+p$ can be said to be in agreement with the projection data p.

Now the generalized inverse $P^+$ can be rewritten as $P^+=B(PB)^+$. This equality results from a property of the generalized inverse operator and the fact, that B is the adjoint of P, as explained above and below. Hence, the minimal norm solution to Pf=p for measured projection data p is given by $f^+=P^+p=B(PB)^+p$. This shows that an image reconstructed according to the expression B(Xp) is in agreement with the measured projection data p, if the filter operator X is embodied as $(PB)^+$. Thus, improved image quality is obtained by the present invention.

In other words, in this embodiment the filter operator X may be entirely, solely, purely and/or directly defined by the certain mathematical description of the tomography geometry which was used when the projecting data p were generated during a limited angle tomography. In other words the filter operator X may be entirely mathematically defined by the geometry which was used for generating the data p. Consequently, heuristic determinations of X are avoided by the present invention. It may be understood that each spatial geometry which is applicable for a limited angle tomography may correspond to one filter X.

As will be described later on, also additional steps may be performed like e.g. regularizing steps which change the character of the filter X from being purely mathematically defined into a mixed character, i.e. being firstly mathematically defined and being secondly amended by e.g. regularizing. For example the ideal filter operator $(PB)^+$ may be amended such that small values in the matrix are exchanged by 0 to ease the calculation. Also the step of suppressing high frequencies may be performed as a regularizing step.

The projection operator PB may comprise at least one convolution of two mathematical functions. When transforming said projection operator PB via Fourier transformation into frequency space, the transformed projection operator P comprises several multiplications of mathematical functions. Due to the transformation of the projection operator PB into frequency space a very efficient calculation of the desired reconstructed image is provided by the present invention. This will be explained hereinafter in more detail. By said transformation, the representation of the projection operator PB is simplified and computational effort of the reconstruction is reduced by the present invention. Details and advantages thereof will be described and will become clearer hereinafter.

It shall be understood that according to the present invention the numerical calculation of the operators P and B is not mandatorily necessary. Only for the determination of PB, specifically for the analogon of PB in frequency space, calculations are necessary. Explicitly calculating P itself may not be necessary for the present invention. B is used for performing the back projection at the end of a method according to an exemplary embodiment of the invention. However, also for B numerical calculations are not mandatorily necessary.

According to another exemplary embodiment the projection operator P as used above and below may be defined by line integrals through the object function O. More concretely, P consists of projection operators $P_1, P_2, \ldots, P_N$, with N denoting the number of projections obtained. Each $P_i$ describes one single projection of the object function O and is defined by line integrals through the object function O. In vector notation P can then be written as $P=(P_1, P_2, \ldots, P_N)^t$. The back projection operator B as used above and below is then uniquely defined as the adjoint operator to P. In vector notation it can be defined as $B=(B_1, B_2, \ldots, B_N)$, where for every i $B_i$ is the adjoint vector or matrix of $P_i$.

The adjoint vector or matrix of a given vector can be readily derived by a person skilled in the art.

This means amongst other, that the used filter operator $X=(PB)^+$ is defined by all the projections obtained during the limited angle tomography. In other words the filter operator $(PB)^+$ as it may be used in an exemplary embodiment of the present invention is based on all N projections obtained upon generating data p.

According to another exemplary embodiment of the invention, the method further comprise the step of performing a Fourier transformation of the projection data p along a trajectory of a radiative source, which trajectory was used for the generation of projection data p, multiplying values of all N projections regarding an electromagnetic frequency component k with the filter operator to form multiplied data Xk, and performing an inverse Fourier transformation of the multiplied data Xk. The electromagnetic frequency component may be seen as a component of the spectrum which has been detected during the generation of the limited angle tomography data p.

The k components of each projection of the N projections may be represented e.g. as a vector which is then multiplied with the Matrix $X=(PB)^+$. Also other mathematical representations are possible.

This may be repeated for all or essentially all frequency components.

According to another exemplary embodiment of the invention, the method further comprise the step of providing geometry data d describing the certain tomography geometry used for the generation of the projection data p.

For example, the geometry data d may comprise a number of projections i.e. a number of views that were generated during the limited angle tomography which generated the projection data p. Additionally or alternatively, the covered angular range of the performed limited angle tomography may be stored in the geometry data d. Also other parameters may be stored in said data set d.

The geometry data d may be generated by a tomography device which performs the limited angle tomography. Said data may be stored and/or transmitted to a calculation device which performs the method of the present invention. If desired, the tomography device itself uses the geometry data d in order to perform the method of the present invention, such that a reconstructed image of the analysed object O is generated. Such a reconstructed image of the object O may be displayed to a user on a display, which is part of the tomography device or the calculation device. This applies to this and every other embodiment of the present invention.

According to another exemplary embodiment of the invention, the provided geometry data describing the certain tomography geometry are the basis for the calculation of the filter operator X.

In other words, according to this exemplary embodiment of the invention the filter operator X is calculated based on the geometry data d. In other words, the filter operator X is purely mathematically defined by the geometry data d. As described above and below, the geometry data d may for example comprise the number of projections and/or the covered angular range of the performed limited angle tomography.

According to another exemplary embodiment of the invention, the method comprises the steps of calculating a projection operator P, calculating a back projection operator B, generating a composed operator PB, generating a generalized inverse operation $(PB)^+$, wherein the generalized inverse operator $(PB)^+$ is used as the filter operator X, as described above and hereinafter. Furthermore, this exemplary embodiment of the invention comprises the step of applying the generalized inverse operator $(PB)^+$ as filter operator to the projection data p to create the filtered projection data $(PB)^+p$. In this embodiment the step S3 of calculating a back projection generates the reconstructed image of the object, which reconstructed image is named as $B(PB)^+p$.

If desired, the source of the limited angle tomography process is moved over the fixed detector along either rows or columns of the detector. In this and any other exemplary embodiment of the invention, the movement of the radiative source relative to the detector may be in a straight line or may also be circular. In order to provide for a calculation of the filter X it might be important, that the radiative source moves within a plane, which is perpendicular to the plane defined by the detector. Thus, the trajectory of the radiative source may be a straight line at a constant height above the detector.

Thus, the presented method makes use of a special tomography geometry which allows for the sufficient calculation of a high quality solution as a high quality reconstructed image.

Therein, the presented method achieves that the reconstructed image is in accordance with the projection data although the projection data are from a limited angle tomography and may thus be regarded as incomplete. In other words, the used filter operator X of the present invention has a direct and well-defined dependency with regard to the spatial geometry, with which the projection data p have been recorded. The presented method does not determine the filter operator X iteratively but directly determines the filter operator X. Furthermore, the present invention does not determine the solution of the underlying mathematical problem iteratively, but determines the solution, i.e. a high quality reconstructed image directly.

The enabled high velocity of the calculation of the present invention is caused inter alia by the insight to the above and below described special tomography geometry used within the limited angle tomography. This geometry may be seen as a perpendicular geometry. Then filter operator X can be composed by P and B, wherein projection operator P might have already been transformed via Fourier transformation into the frequency space. Furthermore, the generalized inverse of said composed operator PB can be generated, $(PB)^+$. This may be seen as the filter operator $(PB)^+$ which is applied to the incomplete data p, created during a limited angle tomography. In case the radiative source is moved within a plane which is perpendicular to the plane defined by the detector, the present invention gains from a possible efficient mathematical determination of $(PB)^+$.

If desired the resulting reconstructed image may be displayed to a user. If desired resulting reconstructed image may be compared with another image generated by a known iterative reconstruction method like e.g. SART.

In the case of a limited angle tomography by means of e.g. a CT the trajectory of the used radiative source, i.e. for example a X-Ray source, can be defined within a plane, which plane is perpendicular to the plane defined by the sensor or detector elements. The present invention provides inter alia for the insight that in such a case the filter operator X which is applied to the projection data p provides for several advantages if embodied as generalized inverse operator $(PB)^+$.

In case of such a certain tomography geometry as the beforehand described trajectory of the source of the limited angle tomography, the composed operator PB can mathematically be represented as a composed operator comprising mathematical convolutions. If performing the projection operator PB via Fourier transformation into the frequency space, the advantage can be used that PB is mathematically represented by multiplications of the convoluted functions. This may result in an efficiency gain in calculating the reconstructed image due to the present invention. The inventors of the present invention discovered that using the generalized inverse composition operator $(PB)^+$ provides for an image reconstruction for filtered back projection which is fast and delivers image quality that may be as high as the image quality of known iterative reconstruction methods. Furthermore, artifacts within the reconstructed image are significantly reduced by the present invention.

In other words, the represented exemplary embodiment of the invention provides for a filtered back projection with an inventive filter operator X which directly and solely depends on the used tomography geometry during the limited angle acquisition resulting in the projection data p. Therefore, for a given acquisition geometry the composed operator PB may only be calculated once in time. In other words, different objects may be analyzed or observed by the limited angle tomography and the same method and the same operator X, e.g. embodied as the generalized inverse composition operator $(PB)^+$, can be used for these and different measurements. This advantage of the present invention makes the direct and defined dependency of the filter operator X from the certain tomography geometry used for the limited angle acquisition clear.

According to another exemplary embodiment of the invention, the filter operator X comprises the composed operator PB, wherein the operator PB is a composed operator comprising/consisting of at least one convolution of two mathematical functions.

Such a representation of the projection operator PB of the present invention takes advantages from the possibility to transform such an operator into the frequency space. The corresponding representation in the frequency space of said composed projection operator P comprises several multiplications of said mathematical functions. This simplifies the calculation that needs to be done in order to generate the reconstructed image of the object O.

According to another exemplary embodiment of the invention, the method comprises the step of transforming the projection operator PB by means of a Fourier transformation into frequency space wherein the projection operator PB transformed into the frequency space comprises/consists of several multiplications of mathematical functions.

In the following the advantageous and efficient calculation of the filter $(PB)^+$ in frequency space is explained.

In case the radiative source is moved on a straight line parallel to the plane defined by the detector, a very efficient mathematical determination of $(PB)^+$ is possible. In the more general setting in which the radiative source is moved within a plane which is perpendicular to the plane defined by the detector, the setting described in the previous setting can be used as an approximation for an efficient determination of $(PB)^+$. The usage of the approximated setting generally causes only low loss of accuracy in the reconstructed image. This amount of loss in accuracy depends on how much the trajectory on which the radiative source is moved differs from a straight line parallel to the plane of the detector. The present invention makes use of this insight.

For the setting of the radiative source being moved on a straight line parallel to the plane defined by the detector, which can be used to approximate the more general settings as explained above, the efficient mathematical determination of $(PB)^+$ can be performed as described in the following. First, it is noted that the described setting of the source being moved on a straight line parallel to the plane defined by the detector allows treating the three-dimensional reconstruction problem as a set of two-dimensional problems. These correspond to the two-dimensional, where each such plane is defined by the straight line of the source trajectory and a straight line on the detector parallel to the source trajectory. Hence, for reconstruction it suffices to consider the corresponding two-dimensional problems. The above described definitions of the operators P and B as $P=(P_1, P_2, \ldots, P_N)^t$ and $B=(B_1, B_2, \ldots, B_N)$ result in a composed operator PB that can be written as a matrix with entries being the composed operations $P_i B_j$, for $i,j=1, \ldots, N$. In the case that the source trajectory has constant height over the detector, each such operation $P_i B_j$ can be described as a convolution with a convolution kernel of bounded support. This description of $P_i B_j$ as a convolution is illustrated in the below described FIG. 8. The operations $P_i B_j$ can now be transformed into frequency domain. Due to the convolution theorem, in frequency domain the operations $P_i B_j$ are represented by multiplications. For the discrete versions of the operations $P_i B_j$, which will be used for the numerical filter calculation, this means that they are represented by diagonal matrices. This representation by diagonal matrices means significant gain of efficiency when calculating the filter X as the generalized inverse $(PB)^+$. In fact, due to the sparse representation of the matrix PB, it is possible to gain a factor of $M^2$ in the calculation of $(PB)^+$, which can be performed e.g. by singular value decomposition. Here M denotes the number of detector pixels per row. This insight of the present invention enables for a faster image reconstruction.

FIG. 8 gives a graphical description of this convolution operation for the case of a planar detector and a straight line of sources positions which can also be described as a two-dimensional problem.

Furthermore, the sparse representation of PB results in a sparse representation of $(PB)^+$. This provides that the filtering of the projection data described by $(PB)^+p$, with p the measured projection data, can be performed efficiently. In this step, the sparse representation of $(PB)^+$ allows for saving a factor M in numerical complexity. This saves important time.

In view of the above an advantageous exemplary embodiment of the invention defines that the data p are obtained upon a movement of the radiative source on a trajectory with a constant height over a detector, and each element $P_iB_j$ of $(PB)^+$ is described as a convolution of at least two mathematical functions.

According to another exemplary embodiment of the invention, the projection data p describe an angular range covered by the limited angle tomography. Said limited angle tomography is the process by means of which the used projection data p has been generated. Furthermore, the angular range covered by the limited angle tomography is smaller than 180 degrees.

This embodiment represents a method of limited angle tomography. Due to several reasons, the object O which is to be analyzed by the tomography can only be radiated with electromagnetic radiation from the source from an angular range smaller than 180 degrees. In such a case, the presented method clearly realizes the above and below described advantages.

According to another exemplary embodiment of the invention, the method comprises the step of performing a limited angle tomography to generate projection data p wherein in this step comprises the following further steps; providing for a radiative source and a corresponding detector, wherein the detector defines a detection plane. A further step of moving the radiative source relative to the detector is comprised wherein the source is moved within a plane which is perpendicular to the detection plane. Furthermore, the step of detecting projection signals by the detector thereby generating the projection data p is performed by means of the presented embodiment.

In other words, a complete limited angle tomography process is represented by this exemplary embodiment of the present invention. Furthermore, a limited angle tomography in combination with a filtered back projection according to the present invention is provided. If desired, only a special region of interest may be reconstructed by means of the present invention. Therefore, an accelerated and shortened limited angle tomography is possible with regard to only a specific region of interest of the object. Such a region of interest reconstruction for limited angle tomography will be described hereinafter in more detail. In short, this embodiment provides for a fast filtered back projection method which is able to handle incomplete projection data p generated by a limited angle tomography resulting in image quality comparable with that of complicated iterative methods, wherein the present invention allows for region of interest reconstruction.

According to another exemplary embodiment of the invention, the geometry data d describe at least a trajectory of the radiative source of a limited angle tomography. If desired, the trajectory of the source relative to the radiation detector is described by the geometry data d. Therein the trajectory of the source described in the geometry data d may lie within a plane which is perpendicular to a detector plane used in the limited angle tomography. If desired, said plane perpendicular to the detector plane may extend trough rows or columns of the detector element.

According to another exemplary embodiment of the invention, the method further comprises the step of regularizing the projection data p.

As the provided projection data p may comprise mistakes due to several reasons, a regularization step may be provided, if desired, by the user. Furthermore, the step of regularizing may lead to a comparability of the results of the presented method, i.e. of the quality of the reconstructed image of the object O, with regard to results of the prior art like for example known SART. For example, it may be defined how many iteration steps n of the prior art SART iteration might be need to provide good quality image results. This may be seen as a regularizing step within the prior art method of SART.

In contrast to said prior art SART reconstruction, the present invention does not need several iteration steps. The application of the filter operator X to the projection data p as well as forming a back projection with the back projection operator B needs only one iteration and thus provides for a direct solution of the underlying mathematical problem. In other words, the present invention provides for a direct and non-iterative way of reconstructing an image by means of a unique and advantageous filter operator X.

According to another exemplary embodiment of the invention, the method comprises the step of delimiting the back projection operator B on a desired region of interest. This may be done by e.g. an user or may also be done e.g. automatically by a program element or e.g. by a computer. Furthermore, the step of calculating the back projection is performed with the delimited back projection operator. In other words the filtered projections are back projected to only the desired reconstruction volume.

In other words, this presented embodiment of the invention enables a region of interest reconstruction in limited angle tomography. Low computational effort is needed and the quality of the generated image, i.e. the reconstructed image of object O, is equivalent to the results of known iterative reconstruction methods. Therefore, the present exemplary embodiment realizes on the one hand the advantage of a filtered back projection method, the ability to reconstruct only region of interests of the object, and on the other hand the advantage of iteratively construction methods i.e. providing for a good reconstruction image quality.

Such an embodiment may be seen in FIG. 5. It provides for fast image reconstruction and provides for the advantages of FBP reconstruction, namely voxel size and reconstruction field of view (FOV) and ROI can be chosen arbitrarily by the user. The main computational effort may lie in the step back projecting which needs to be executed only once for the ROI. This is in contrast to iterative reconstruction like SART of the prior art, where the back projection and the projection has to be performed in each iteration for the full FOV and ROI.

In other words, the presented embodiment of the invention provides for a faster image reconstruction than iterative reconstruction and it simultaneously produces equivalent image quality.

According to another exemplary embodiment of the invention, the method further comprises the step of delimiting the projection data p to a delimited input for the filter operator X.

Thus, the presented embodiment provides for a selective back projection.

According to another exemplary embodiment of the invention the method further comprises the step of performing zero padding.

More details about said zero padding step can be gathered from Chapter 3 in A. Kak and M. Slaney, The Principles of Computerized Tomography, IEEE Press, New York, USA, 1999.

According to another exemplary embodiment of the invention the method further comprises the step of continuing projections of the data set p, which projections were cut during the generation of the data set p.

Additional details about said step of continuing projections can be found in LEWITT R., <<Processing of incomplete measurement data in computed tomography>>, Med. Phys., vol. 6, no 5, pp. 412-417, 1979.

According to another exemplary embodiment of the invention, a calculating device for an image reconstruction for a filtered back projection in limited angle tomography is presented. The calculation device comprises the calculation unit configured to calculate a filter operator X, wherein the calculation unit is configured to calculate filtered projection data Xp upon applying the filter operator X on limited angle tomography projection data p such that Xp describe N filtered projections of the object and wherein each filtered projection is calculated from all N projections of the data p. Furthermore the calculation unit is configured to calculate a back projection B(Xp) of the filtered projection data Xp to generate a reconstructed image of the object O.

The calculating device may be embodied by a computer or a processor. The calculating device may be a separate physical element or may also be integrated in, for example, a tomography like e.g. a CT or a breast mammographic device. For example, the calculating device may be part of a tomograph which performs limited angle tomography such that the tomograph gains from the above and below presented advantages of the present invention. Furthermore, the calculation unit may be embodied as for example a processor in a computer or in a tomograph. It shall exemplarily be mentioned that for example C-arm tomographic systems, conventional CTs, swing trajectory devices, tomography devices performing tomosynthesis and devices applying tomosynthesis for RAD application may be seen as calculation devices which make use of the present invention. Therefore, the aforementioned devices may be equipped with a calculation unit as defined within the previously presented exemplary embodiment of the invention.

According to another exemplary embodiment of the invention, a computer-readable medium in which a computer program for imaging reconstruction for a filtered back projection in limited angle tomography is stored, which computer program when been executed by a processor is adapted to carry out obtaining projection data p of an object O, wherein the projection data p describes N projections of the object O, which N projections were generated with the certain tomography geometry of a limited angle tomography. Applying a filter operator X to the projection data p to generate filtered projection data Xp, wherein Xp describe N filtered projections of the object and wherein each filtered projection is calculated from all N projections of the data p. And calculating a back projection of the filtered projection data Xp using a back projection operator B to generate a reconstructed image B(Xp) are further steps that are carried out as defined above.

In other words upon the step of applying X to p all N projections of the data p are filtered and combined to generate filtered projection data Xp.

According to another exemplary embodiment of the invention, a program element for image reconstruction for a filtered back projection in limited angle tomography is presented, which element, when being executed by a processor, is adapted to carry out receiving projection data p of an object O, wherein the projection data p describes the projections of the object O, which projections were generated with the certain tomography geometry of a limited angle tomography. Applying a filter operator X to the projection data p to generate filtered projection data Xp, wherein Xp describe N filtered projections of the object and wherein each filtered projection is calculated from all N projections of the data p. And calculating a back projection of the filtered projection data Xp using a back projection operator B to generate a reconstructed image B(Xp) are further steps that are carried out as defined above.

In other words the filtered projection data Xp describe N filtered projections. Each of these filtered projections is calculated from all projections of the limited angle tomography data set p by applying the filter X to each of these projections before combining them into each filtered projection. In this way, each filtered projection depends on all other projections which have been acquired as a part of this limited angle tomography projection data set.

In other words upon the step of applying X to p all N projections of the data p are filtered and combined to generate filtered projection data Xp.

The computer program element may be part of a computer program, but it can also be an entire program by itself. For example the computer program element may be used to update an already existing computer program to get to the present invention.

The above presented features and other features of the invention will become apparent from and elucidated with reference to the embodiments described hereinafter.

BRIEF DESCRIPTION OF THE DRAWINGS

Exemplary embodiments of the invention will be described in the following drawings. In principle, identical parts are provided with the same reference symbols in the figures.

DETAILED DESCRIPTION OF EMBODIMENTS

Figure 1:
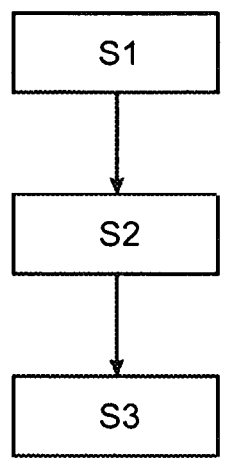
FIGS. 1 to 5 schematically show different flow diagrams of different methods according to different exemplary embodiments of the present invention.

FIG. 1 shows method steps S1 to S3 and thereby describes a method of image reconstruction for a filtered back projection in limited angle tomography according to an exemplary embodiment of the present invention. As a first step projection data p of an object O are provided within step S1. The projection data p describes N projections of the object O, which N projections were generated with the certain spatial tomography geometry during performing a limited angle tomography. Therein N is an integer like e.g. 1, 2, 3, 4, and so on. Applying a filter operator X to the projection data p to generate filtered projection data Xp is performed within step S2, wherein Xp describe N filtered projections of the object and wherein each filtered projection is calculated from all N projections of the data p. Subsequently, the calculation of a back projection of the filtered projection data Xp using a back projection operator B to generate a reconstructed image B(Xp) is shown in FIG. 1 in S3. For example the filter operator X may be embodied as generalized inverse operator $(PB)^+$ or as an amended generalized inverse operator $(PB)^+$ as described above.

The filtered projection data Xp describe N filtered projections. Each of these filtered projections is calculated from all projections of the limited angle tomography data set p by applying the filter X to each of these projections before combining them into each filtered projection. In this way, each filtered projection depends on all other projections which have been acquired as a part of this limited angle tomography projection data set.

In case no approximations are included, the filter operator X may be purely mathematically defined by the certain spatial tomography geometry with which the projection data p was generated. However, if desired, the present invention may also include approximations like regularizing steps as described above and hereinafter.

Thus, heuristic determinations of X are avoided by the present invention. The embodiment of the filter operator X allows for obtaining an image f that is in agreement with all the projection data p, i.e. an image f fulfilling the equation Pf=p. This is shown in the following. X may be embodied as $(PB)^+$.

First, the generalized inverse, also known as Moore-Penrose pseudoinverse, is defined for this purpose. For a linear operator P, the generalized inverse operator $P^+$ can be defined as the operator assigning to any p the minimal norm solution $f^+$ of the linear equation Pf=p with unknown f. The minimal norm solution is defined as the unique solution with minimal norm to the said equation. Hence, in the case of p denoting the measured projection data, the minimal norm solution $f^+=P^+p$ can be said to be in agreement with the projection data p. Now the generalized inverse $P^+$ can be rewritten as $P^+=B(PB)^+$. This equality results from a property of the generalized inverse operator and the fact, that B is the adjoint of P, as explained below. Hence, the minimal norm solution to Pf=p for measured projection data p is given by $f^+=P^+p=B(PB)^+p$. This shows that an image reconstructed according to the expression B(Xp) is in agreement with the measured projection data p, if the filter operator X is embodied as $(PB)^+$.

The projection operator P as used above and below may be defined by line integrals through the object function O. More concretely, P consists of projection operators $P_1, P_2, \ldots, P_N$, with N denoting the number of projections obtained. Each $P_i$ describes one single projection of the object function O and is defined by line integrals through the object function O. In vector notation P can then be written as $P=(P_1, P_2, \ldots, P_N)^t$. The back projection operator B as used above and below is then uniquely defined as the adjoint operator to P. In vector notation it can be defined as $B=(B_1, B_2, \ldots, B_N)$, where for every i $B_i$ is the adjoint of $P_i$.

Consequently, the method of FIG. 1 may be seen as a method of performing a limited angle tomography and combining it with an advantageous new variant of special filtered back projection with filter operator $X=(PB)^+$. If desired the step of measuring the angular range of the limited angle tomograph used for the generation of data p may be performed by the present invention. Filter operator X may be calculated entirely mathematically based on the measured angular range.

In other words, the presented method of FIG. 1 achieves that the reconstructed image is in accordance with the projection data p although the projection data are from a limited angle tomography and may thus be regarded as incomplete.

Due to several reasons a tomograph device may not be movable around 180 degrees with regard to the object. For example, such device may only be movable in a limited way. Additionally, a very low dosage of for example X-ray shall be applied in such a procedure. Thus, during limited angle tomography this may lead to an incomplete projection data, in the sense of not-describing projections of the object along 180 degrees. The method of FIG. 1 overcomes said disadvantages as the filtered back projection according to the present invention may be used with incomplete data p.

If desired, the source of the limited angle tomography process is moved over the fixed detector along either rows or columns of the detector according the method of FIG. 1. In this and any other exemplary embodiment of the invention, the movement of the radiative source relative to the detector may be in a straight line or may also be circular. Thus, the presented method makes use of a special spatial tomography geometry which allows for the sufficient calculation of a high quality solution as a high quality reconstructed image.

Consequently, the used filter operator X of the present invention has a direct and well-defined dependency with regard to the spatial geometry, with which the projection data p have been recorded. The presented method does not determine the filter operator X iteratively but directly determines the filter operator X. Furthermore, the present invention does not determine the solution of the underlying mathematical problem iteratively, but determines the solution, i.e. a high quality reconstructed image directly.

The enabled high velocity of the calculation of the present invention is caused inter alia by the insight to the above and below described special tomography geometry used within the limited angle tomography. This geometry may bee seen as a perpendicular geometry. For the calculation of the filter operator X, the composed operator PB can be determined. The composed operator may be defined in spatial or already in frequency domain. Furthermore, the generalized inverse of said composed operator PB can be generated, $(PB)^+$ which equals X. This may be seen as the filter operator $(PB)^+$ which is applied to the incomplete data p, created during a limited angle tomography. In case the radiative source is moved within a plane which is perpendicular to the plane defined by the detector, the present invention gains from a possible efficient mathematical determination of $(PB)^+$.

The method of FIG. 1 may be seen as a limited angle tomography method. By the presented method steps S1 to S3 a solution f to equation P(f)=p is provided as defined by the presented embodiment of the invention. The solution f as provided by the presented embodiment may be seen as the reconstructed image B(Xp) of the object O. As it will be defined later on and as has been defined above, the filter operator X may for example be embodied as $(PB)^+$. However, other filter operators X are possible which depend on the limited angle tomography geometry, i.e. the back projection and/or the covered angular range of the tomography process. But heuristic determinations of X are avoided by the present invention.

Figure 2:
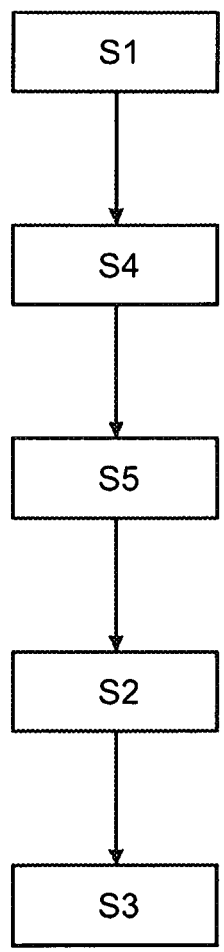

FIG. 2 describes a flow diagram of a method which in addition to FIG. 1 comprises the additional method steps S4 and S5. The advantages and explanations of S1 to S3 can be gathered from the above presented description of FIG. 1. Step S4 describes the provision of geometry data d describing the certain spatial tomography geometry used for the generation of the projection data p. For example, the geometry data d may comprise the number N of projections that are generated during performing the limited angle tomography. Furthermore or alternatively, the geometry data d may comprise the amount of the angular range which was covered by the previously performed limited angle tomography with which data p were generated. Furthermore, other parameters describing the certain tomography geometry may be comprised by data d, if desired.

Based on the provided geometry data d, the filter operator $X=(PB)^+$ is mathematically calculated. This is shown in step S5. In other words, the filter operator X is purely mathematically defined by the spatial geometry which was used during the limited angle tomography in order to produce the projection data p. Consequently, heuristic determinations of X are avoided by the present invention. The filter operator X, which is generated and calculated as described above, is applied during step S2 with the projection data p as already described with regard to FIG. 1. Additionally, the calculation of the back projection as defined in step S3 of FIG. 1 is in analogue way performed in FIG. 2 with filter operator $X=(PB)^+$. If desired the step of measuring the angular range of the limited angle tomograph used for the generation of data p may be performed by the present embodiment.

Figure 3:
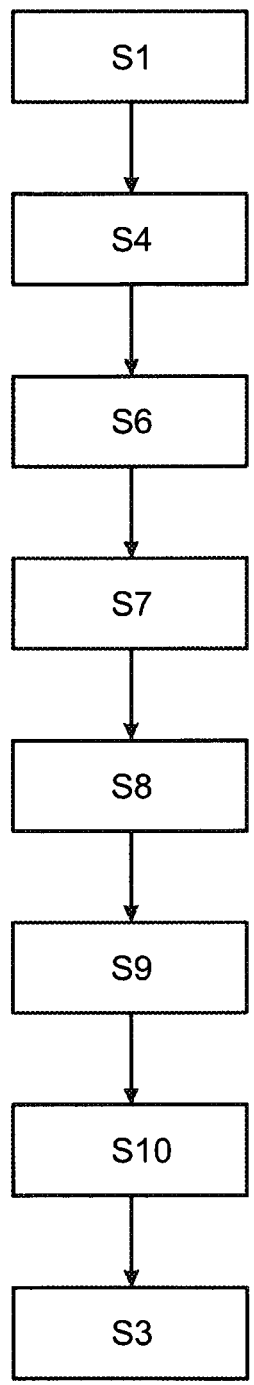

FIG. 3 shows another exemplary embodiment of the method of image reconstruction for a filtered back projection in limited angle tomography with $X=(PB)^+$. As described before, step S1 describes the provision of projection data p of an object O which has previously been analyzed with the limited angle tomograph. Furthermore, the geometry data d has been recorded during the performance of the limited angle tomography, which geometry data d are provided during step S4. If desired the step of measuring the angular range of the limited angle tomograph used for the generation of data p may be performed by the present invention. A calculation device or calculation unit may perform a calculation of the projection operator P within step S6. Subsequently or if desired simultaneously, back projection operator B is calculated in step S7. Subsequently or if desired simultaneously, the composed operator PB is calculated and/or generated in step S8. Furthermore, the generalized inverse operator $(PB)^+$ is generated in step S9, wherein the generalized inverse operator $(PB)^+$ is used as the filter operator X, as described herein. The details of the generation of $(PB)^+$ have been described above. Furthermore, the generalized inverse composition operator $(PB)^+$ is applied as filter operator to the projection data p to create filtered projection data $(PB)^+p$ within step S10. Subsequently, a back projection step may be performed. This is defined as calculating a back projection of a filtered projection data Xp using the back projection operator B to generate a reconstructed image B(Xp) in step S3. Thereby the filter operator $(PB)^+$ is solely mathematically defined by the certain spatial tomography geometry with which the projection data p were generated. Thus X is based on the geometry data d.

It shall be understood that according to the present invention the numerical calculation of the operators P and B is not mandatorily necessary. Only for the determination of PB, specifically for the analogon of PB in frequency space, calculations are necessary. Explicitly calculating P itself may not be necessary for the present invention. B is used for performing the back projection at the end of a method according to an exemplary embodiment of the invention. However, also for B numerical calculations are not mandatorily necessary.

The method of FIG. 2 ensures that Xp describe N filtered projections of the object and wherein each filtered projection is calculated from all N projections of the data p. Therefore the presented method provides for a higher stability against noise and provides for a correct consideration of redundant data.

Thus, FIG. 3 depicts a flow diagram of filtered back projection method which uses a very special filter operator $X=(PB)^+$. The presented method makes use of the circumstance that in limited angle tomography special trajectories of the radiative source relative to the detector may advantageously be used. Said trajectory is defined to lay inside a plane which is perpendicular to the plane that is defined by the detector elements. These detector elements can be gathered from the following FIG. 7. The filter operator X, as defined in the present invention, provides for several advantages like for an accelerated image reconstruction with a comparable quality compared to a known techniques like e.g. SART reconstruction.

The composed operator PB may comprise at least one convolution of two mathematical functions. When transforming said composed operator PB via Fourier transformation into frequency space, the transformed projection operator P comprises several multiplications of mathematical functions. Due to the transformation of the composed operator PB into frequency space a very efficient calculation of the desired reconstructed image is provided by the present invention. This will be explained hereinafter in more detail. By said transformation, the representation of the composed operator PB is simplified and computational effort of the reconstruction is reduced by the present invention. Details and advantages thereof will be described and will become clearer hereinafter.

In the context of the present invention limited angle tomography projection data p was/were generated with a tomography using less than 180° around the object like e.g. a human breast which is analyzed with the tomography.

Figure 4:
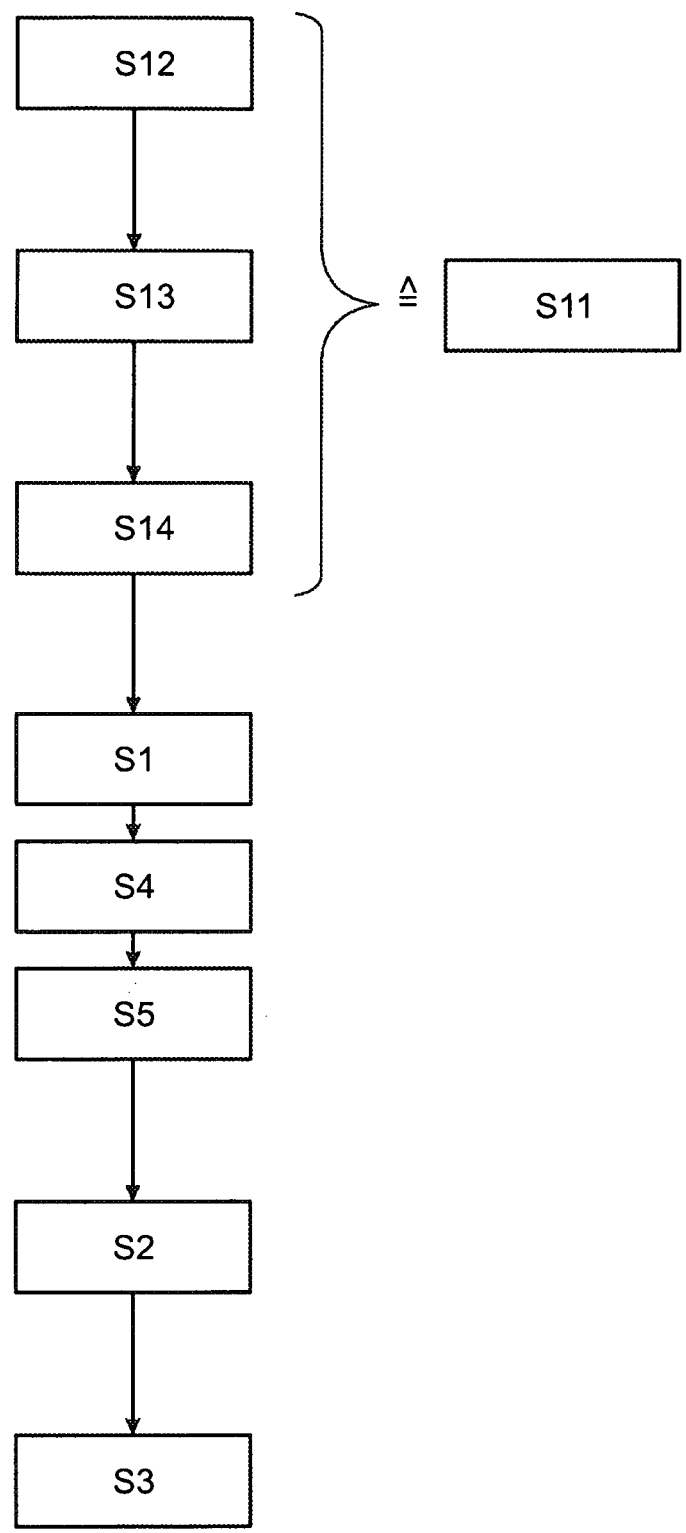

FIG. 4 shows another flow diagram of a limited angle tomography method comprising a filtered back projection according to another exemplary embodiment of the present invention. The shown method is for image reconstruction by a filtered back projection. Before the reconstruction process is be performed as described above and below, a limited angle tomography is performed in order to generate the incomplete projection data p. The term "incomplete data p" may be understood in the sense that p describes projections of the object O along angular range that is smaller than 180 degrees. This can be gathered from the following FIG. 7.

Furthermore, FIG. 4 shows step S11 describing the step of performing a limited angle tomography to generate the projection data p. As can be seen in FIG. 4, step S11 comprises the three steps S12 to S14. The step S12 depicts providing for a radiative source and a corresponding detector. The detector defines a detection plane. Furthermore, the step of moving the radiative source relative to the detector is depicted in FIG. 4 with S13. Thereby the source is moved in a plane which is perpendicular to the detection plane. Furthermore, step S14 is performed, wherein S14 describes detecting projection signals by the detector and thereby generating the incomplete projection data p. Subsequently or simultaneously, the steps S1, S4, S5, S2 and S3 are performed and have been described before with regard to FIGS. 1 and/or 2.

Figure 5:
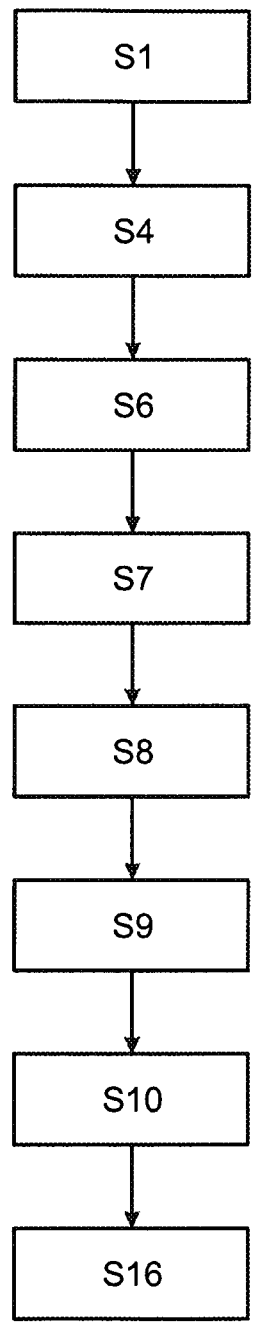

FIG. 5 shows another flow diagram of a method according to another exemplary embodiment of the invention. FIG. 5 depicts a limited angle tomography process in combination with a filtered back projection of only a special region of interest. Thus, only the region of interest is reconstructed. Therefore, an accelerated and shortened limited angle tomography is possible with regard to only the specific region of interest of the object O. Regarding the steps from S1 to S10 it is referred to the description of FIG. 3. Embodiment of FIG. 5 may apply the same steps as described above regarding FIG. 3. However, the embodiment of FIG. 5 does not perform step S3 after S10 but performs step S16. Step S16 describes the steps of delimiting the back projection operator B on a desired region of interest by a user, wherein the step of calculating a back projection S3 is performed with the delimited back projection operator. In other words, the embodiment of FIG. 5 enables for a region of interest for reconstruction for limited angle tomography thereby providing for equivalent image results compared to state of the art iterative construction methods. The reconstruction method of FIG. 5 is fast and provides for the advantages of FBP reconstruction, namely voxel size and reconstruction field of view (FOV) and region of interest (ROI) can be chosen arbitrarily by the user. The main computational effort may lie in the step back projecting which needs to be executed only once for the ROI. This is in contrast to iterative reconstruction like SART of the prior art, where the back projection and the projection has to be performed in each iteration for the full FOV and ROI.

In other words, the presented embodiment of the invention provides for a faster image reconstruction than iterative reconstruction and it simultaneously produces equivalent image quality. The method of FIG. 5 realizes that Xp describe N filtered projections of the object and wherein each filtered projection is calculated from all N projections of the data p. Therefore the presented method provides for a higher stability against noise and provides for a correct consideration of redundant data.

In any of the above described methods of FIGS. 1 to 5 the following steps may additionally be performed. Performing a movement of the radiative source on a trajectory with a constant height over a detector upon which movement the data p are generated, wherein each element $P_iB_j$ of $X=(PB)^+$ comprises a convolution of at least two mathematical functions.

Furthermore each element $P_iB_j$ of $X=(PB)^+$ may consist of a convolution of at least two mathematical functions.

According to yet another exemplary embodiment the following steps may further be comprised: transforming the projection operator PB by means of a Fourier transformation into frequency space, wherein the projection operator PB transformed in frequency space comprises several multiplications of mathematical functions. This realizes the decrease in calculation time as described above in detail.

Furthermore the projection operator PB transformed into frequency space may consist of several multiplications of mathematical functions.

Figure 6:
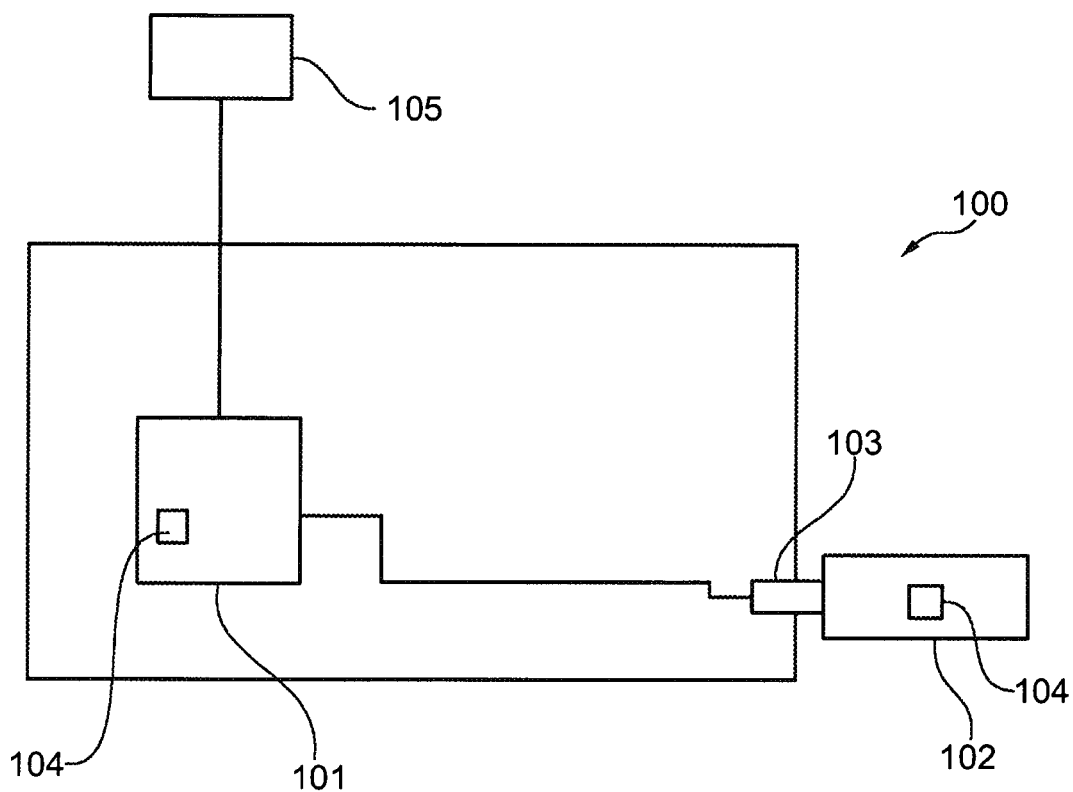
FIG. 6 schematically shows a calculation unit according to another exemplary embodiment of the present invention.

FIG. 6 schematically shows a calculating device 100 for image reconstruction for a filtered back projection in limited angle tomography. The calculating device 100 comprises a calculation unit 101. The calculation device 100 may be embodied for example as a computer or any tomographic device as e.g. C-arm tomographic system, a conventional CT using X-Rays, a swing trajectory device, a tomography device performing tomosynthesis or a device applying tomosynthesis for RAD application. The calculation unit 101 may be embodied as e.g. a processor. Furthermore, the calculation unit, shown in FIG. 6, stores a program element 104 which is adapted to carry out the above and below presented methods. The calculation unit 101 may executed said methods. In addition, a display 105 is shown in order to display the reconstructed image of the object O to the user. Furthermore, a computer-readable medium 102 embodied as a USB stick is shown in FIG. 6. Computer-readable medium 102 also comprises the program element 104. An interface 103 is comprised by the calculation device 100. If desired, such a calculation device may be integrated in a medical imaging device like a tomograph in order to perform the desired limited angle tomography and to gain from the advantages of the presented back projection method with the special filter operator X as described above and below.

The calculation unit is configured to use a filter X such that the filtered projection data Xp describe N filtered projections. Each of these filtered projections is calculated from all projections of the limited angle tomography data set p by applying the filter X to each of these projections before combining them into each filtered projection. In this way, each filtered projection depends on all other projections which have been acquired as a part of this limited angle tomography projection data set. Therefore the presented the calculation unit provides for a higher stability against noise and provides for a correct consideration of redundant data.

Figure 7:
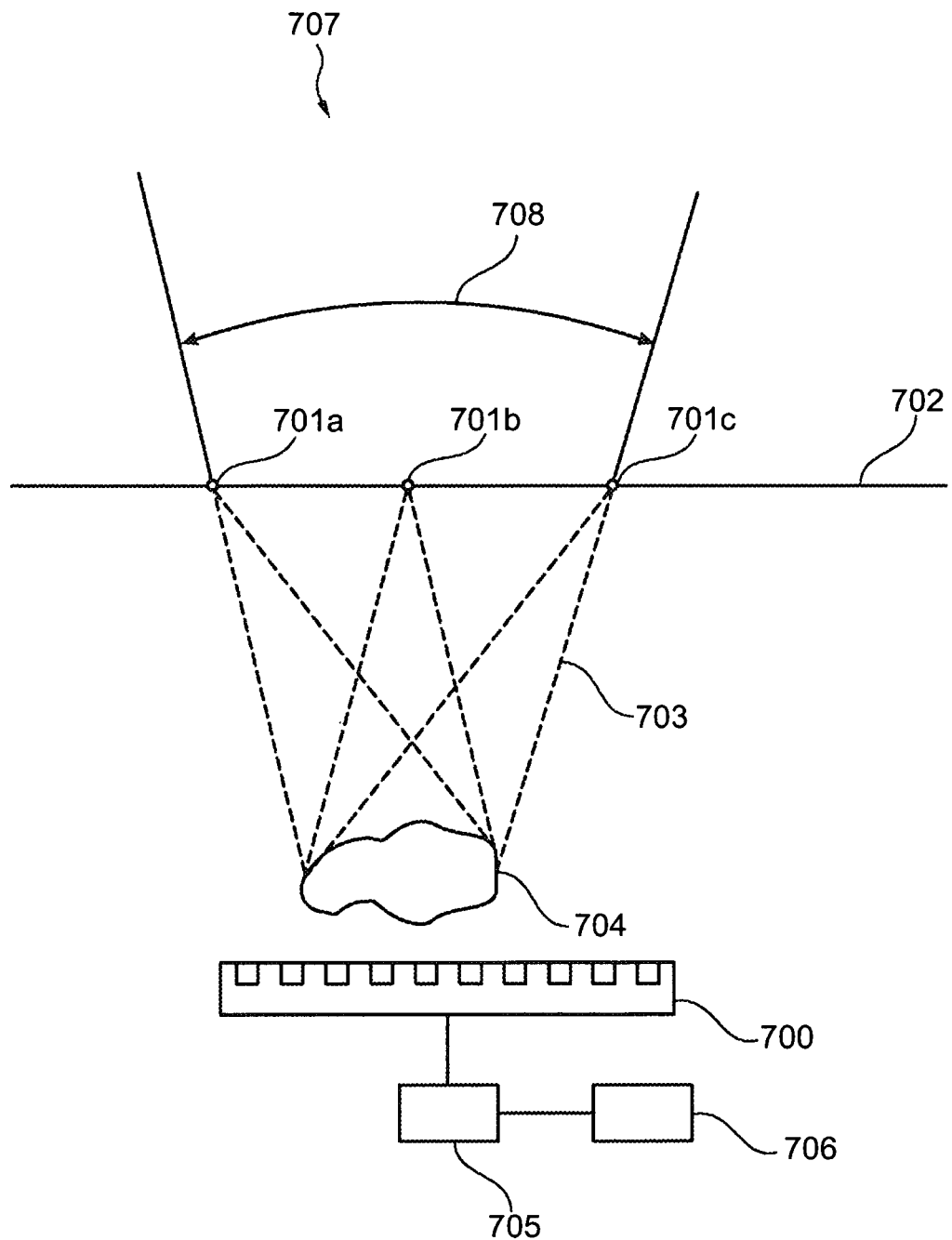
FIG. 7 schematically shows a limited angle tomograph according to another exemplary embodiment of the present invention.

FIG. 7 shows a tomograph 703 for performing a limited angle tomography. Reference sign 708 depicts the limited angular range smaller than 180° leading to an incomplete data set p. A detector 700 is shown above which the object 704 is conditioned. Detector 700 comprises several detector elements arranged in rows and columns as known by the person skilled in the art. The radiative source is exemplarily shown in three different spatial positions 700a, 700b, 700c. All these positions from which projections of the object 704 are generated are positioned along a spatial line 702. However, also other trajectories of the radiative source of the tomograph are possible, as described above. The emitted radiation is exemplarily shown by dotted lines 703. A calculation unit 705 is shown in FIG. 7, which is connected to the detector 700. The calculation unit may generate the projection data p and also the geometry data d, as defined in the Claims and as described above with respect to FIGS. 1 to 6. Furthermore, a display 706 is shown in order to display the generated reconstructed image for example $B(PB)^+p$, to the user or to store the image somewhere.

Due to several reasons a tomograph device may not be movable around 180 degrees with regard to the object. For example, such device may only be movable in a limited way. Additionally, a very low dosage of for example X-ray shall be applied in such a procedure. However, during limited angle tomography this may lead to an incomplete projection data, in the sense of not-describing projections of the object along 180 degrees.

The tomograph 703 compensated said boundary condition by applying the present invention as described herein. Tomograph 703 may be seen as C-arm tomographic system, a conventional CT using X-Rays, a swing trajectory device, a tomography device performing tomosynthesis or a device applying tomosynthesis for RAD application. Thus, a gist of the present invention is to combine the advantages of known iterative methods and of known back projection methods by means of new and inventive subject matter as defined in the independent claims. The present invention makes it possible to use back projection in limited angle tomography, although only incomplete projection data are provided, i.e. projection data which are generated when performing a tomography from an angle smaller than 180° regarding the object. This may be seen in FIG. 7. Furthermore the presented method enables a reconstruction of only a region of interest and not of the whole field of view, the whole object. Additionally the presented invention is a very fast and results in a reconstructed image which has a comparable quality compared to the results of known iterative methods. The method of the present invention is not iterative. Said advantages and characteristics of the present invention will become clearer and elucidated from the following description.

Figure 8:
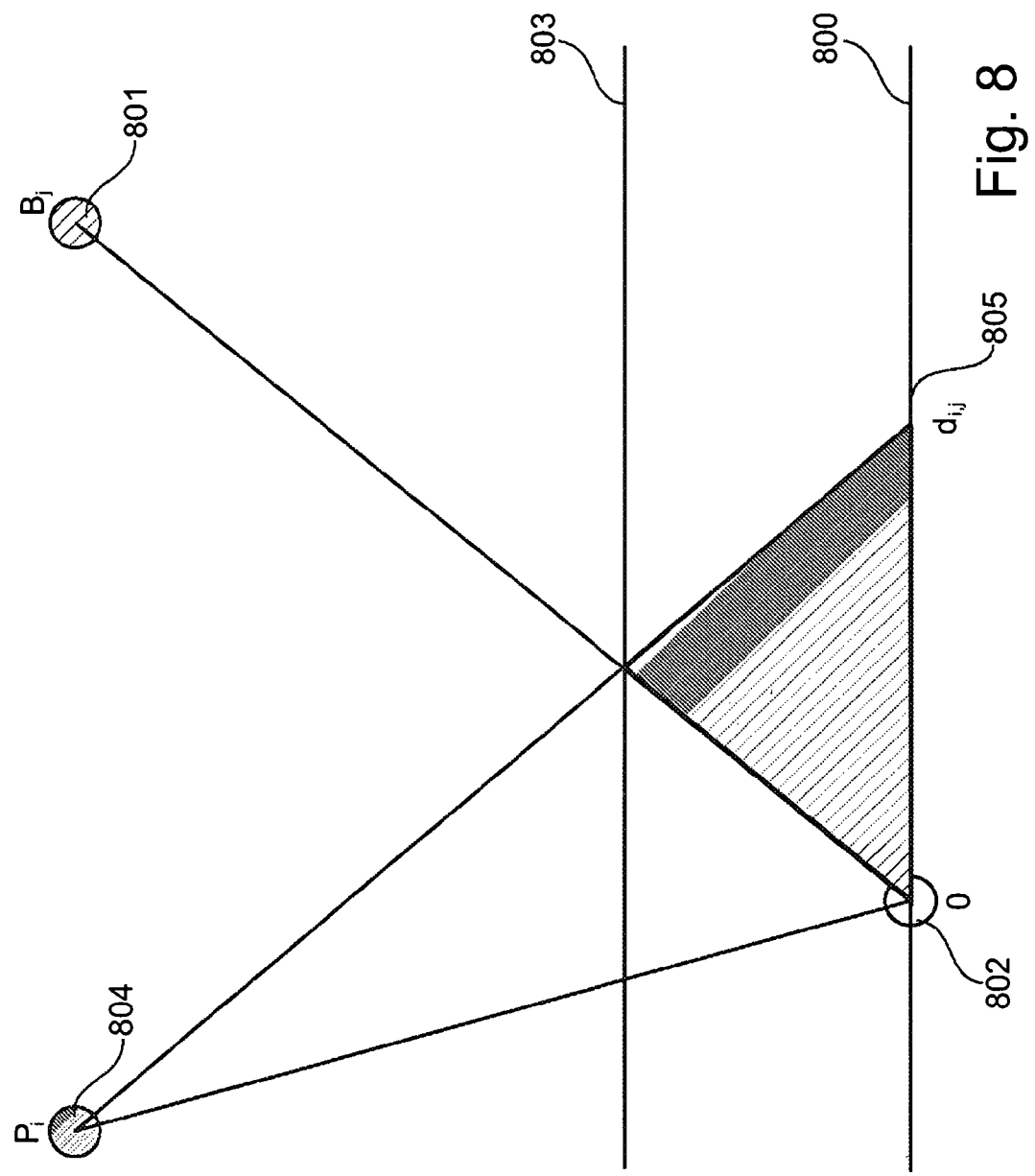
FIG. 8 schematically shows the effect of a back projection and projection operator for the source positions i and j for the case of an object of bounded height in a two dimensional reconstruction problem.

FIG. 8 gives a graphical description of the convolution operation already described above. This is a convolution operation for the case of a planar detector 800 and a straight line of sources positions which can also be described as a two-dimensional problem. The back projection operator $B_j$ 801 back projects a value from the position 0 802 towards the source position j into the image volume resulting in image values along this line. Here the volume is bounded in height above the detector plane as described by the parallel line 803 above the line describing the detector 800. The projection operator $P_i$ 804 forward projects the image values along the line onto the detector pixel between 0 and $d_{i,j}$ 805 and thus represents the bounded support of the convolution.

It may be seen as a further gist of the invention to provide for a method to calculate and/or apply filters for a filtered back projection reconstruction. The filter is calculated in such a way that the resulting FBP image may be equal to an SART image after n iterations from the same projection data set.

The following steps may be involved in the calculation of said filters. Determining the tomography geometry also called system geometry, which may comprise determining the number of views and/or projections and determining the covered angular range used for a limited angle acquisition. If desired more parameters may be determined in order to describe the tomography geometry used for the limited angle acquisition. If desired the equivalent number of iterations for an iterative technique like e.g. SART reconstruction may be set. Therefore, a comparability between the image results of the present invention and the image results of a corresponding SART reconstruction is provided by the presented method.

Furthermore, the step of calculating one or a set of projection filters based on the before mentioned equivalence between SART reconstruction and filtered back projection reconstruction may be performed. Finally, the filtered projections may be back projected to the reconstruction volume.

In other words, the presented method is a general approach to accelerate known techniques like e.g. SART reconstructions for arbitrary acquisition geometries. For a given a tomography geometry i.e. acquisition geometry the composed operator PB of projection operator P and back projection operator B need to be calculated only once. This may lead to a reduction of the time necessary to perform the reconstruction.

The presented method provides for the advantage that the filter i.e. the filter operator like e.g. X, and the composed operator PB can be calculated analytically and depend only on the tomography geometry i.e. the system geometry. If desired, the filters can be made dependent on the equivalent number of SART iterations as described above and hereinafter.

The image reconstruction according to the present invention is fast and provides for the advantages of FBP reconstruction, namely voxel size and reconstruction field of view (FOV) and region of interest (ROI) can be chosen arbitrarily by the user. The main computational effort may lie in the step back projecting which needs to be executed only once for the ROI. This is in contrast to iterative reconstructions like e.g. SART, where the back projection and the projection has to be performed in each iteration for the full FOV and ROI. In other words, the present invention provides for a faster image reconstruction than iterative reconstruction and it simultaneously produces equivalent image quality.

Other variations to the disclosed embodiments can be understood and effected by those skilled in the art in practicing the claimed invention, from the study of the drawings, the disclosure, and the appended claims. In the claims the word "comprising" does not exclude other elements or steps and the indefinite article "a" or "an" does not exclude a plurality. A single processor or other unit may fulfil the functions of several items or steps recited in the claims. The mere fact that certain measures are recited in mutually different dependent claims does not indicate that a combination of these measures cannot be used to advantage. A computer program may be stored/distributed on a suitable medium such as an optical storage medium or a solid-state medium supplied together with or as part of other hardware, but may also be distributed in other forms, such as via the Internet or other wired or wireless telecommunication systems. Any reference signs in the claims should not be construed as limiting the scope of the claims.

The invention claimed is:

1. A method of image reconstruction in limited angle tomography, the method comprising of:
   obtaining limited angle tomography projection data p of an object O, wherein the projection data p describe N projections of the object O, wherein a radiation source is being moved relative to a detector when obtaining the projection data p,
   applying a filter operator X determined non-iteratively as a generalized inverse operator $(PB)^+$, wherein P consists of projection operators $P_1, P_2, \ldots, P_N$, with N denoting the complete projections described by data p, wherein P is represented in vector form as $P=(P_1, P_2, \ldots, P_N)'$, wherein B consists of back projection operators $B_1, B_2, \ldots, B_N$, and wherein B is represented in vector form as $B=(B_1, B_2, \ldots, B_N)$, where for every i $B_i$ is the adjoint of $P_i$, to the limited angle tomography projection data p to generate filtered projection data Xp, wherein Xp describe N filtered projections of the object O and wherein each filtered projection is calculated from all N projections of the data p, and
   calculating non-iteratively a back projection of the filtered projection data Xp using the back projection operator B to generate a reconstructed image B(Xp).

2. The method according to claim 1, further comprising the steps of:
   performing a Fourier transformation of the projection data p along a trajectory of a radiation source, which trajectory was used for the generation of the projection data p,
   multiplying values of all N projections regarding a frequency component k with the filter operator X to form multiplied data Xk, and
   performing an inverse Fourier transformation of the multiplied data Xk.

3. The method according to claim 1, further comprising the steps of:
   providing geometry data d describing the tomography geometry of the limited angle tomography used for the generation of the limited angle tomography projection data p, and
   calculating filter operator $X=(PB)^+$ entirely based on the geometry data d.

4. The method according to claim 1, wherein the data p are obtained upon a movement of a radiation source on a trajectory with a constant height over a detector, and wherein each element PjB, comprises a convolution of at least two mathematical functions.

5. The method according to claim 1, further comprising the step of: transforming the projection operator PB by means of a Fourier transformation into frequency space, and wherein the projection operator PB transformed in frequency space comprises several multiplications of mathematical functions.

6. The method according to claim 1,
   wherein the limited angle tomography projection data p describe an angular range covered by the limited angle tomography, and
   wherein the angular range covered by the limited angle tomography is smaller than 180°.

7. The method according to claim 1, further comprising the steps of:
- performing a limited angle tomography to generate the limited angle tomography projection data p, wherein the performing a limited angle tomography further comprises the steps of:
- providing for the radiation source and the corresponding detector,
- wherein the detector defines a detection plane,
- wherein the source is moved within a plane which is perpendicular to the detection plane, and
- detecting projection signals by the detector upon which detection the limited angle tomography projection data p are generated.

8. The method according to claim 3,
- wherein the geometry data d describe at least a trajectory of a radiation source of a limited angle tomography, and
- wherein the trajectory of the source described in the geometry data d completely lies within a plane which is perpendicular to a detector plane of a detector used in the limited angle tomography.

9. The method according to claim 1, further comprising the step:
- determining a delimited back projection operator B to a desired region of interest- by a user,
- wherein the step of calculating a back projection is performed only once with the delimited back projection operator, which generates a reconstruction of the desired region of interest.

10. A calculating device for image reconstruction for a filtered back projection in limited angle tomography, the calculating device comprising
- a calculation unit configured to calculate a filter operator X determined non-iteratively as a generalized inverse operator $(PB)^+$, wherein P consists of projection operators $P_1, P_2, \ldots, P_N$, with N denoting the complete projections described by data p, wherein P is represented in vector form as $P=(P_1, P_2, \ldots, P_N)^t$, wherein B consists of back projection operators $B_1, B_2, \ldots B_N$, and wherein B is represented in vector form as $B=(B_1, B_2, \ldots, B_N)$, where for every i $B_i$ is the adjoint of $P_i$,
- wherein the calculation unit is configured to obtain limited angle tomography projection data p of an object O, wherein the radiation source is being moved relative to a detector when obtaining the projection data p,
- wherein the calculation unit is configured to calculate filtered projection data Xp upon applying the filter operator X on the obtained limited angle tomography projection data p in such a way that Xp describes N filtered projections of the object O and in such a way that each filtered projection is calculated from all N projections of the data p,
- wherein the calculation unit is configured to calculate a back projection B(Xp) of the filtered projection data Xp to generate a reconstructed image of the object O.

11. The calculating device according to claim 10,
- wherein the calculating device is embodied as a medical imaging device.

12. A non-transitory computer readable medium storing a program element for image reconstruction for a filtered back projection in limited angle tomography, which program element, when being executed by a processor, is adapted to carry out the method according to claim 1.

13. The calculating device according to claim 10, wherein the calculation unit is configured to calculate the back projection B(Xp) as a delimited desired region of interest determined by a user of the filtered projection data Xp to generate a reconstructed image of the object O.

* * * * *